United States Patent
Kendra

(10) Patent No.: US 7,422,106 B1
(45) Date of Patent: Sep. 9, 2008

(54) DISPOSABLE FEMININE PROTECTION STORAGE AND WASTE DISPOSAL SYSTEM

(76) Inventor: Michelle Terese Kendra, 10372 Sutton Pl., Munster, IN (US) 46321

( * ) Notice: Subject to any disclaimer, the term of this patent is extended or adjusted under 35 U.S.C. 154(b) by 78 days.

(21) Appl. No.: 11/106,991

(22) Filed: Apr. 15, 2005

(51) Int. Cl.
*A61B 17/06* (2006.01)
*B65D 81/24* (2006.01)

(52) U.S. Cl. .................................. 206/440; 206/204

(58) Field of Classification Search ............ 206/204, 206/205, 438, 440, 441, 494, 551, 527, 459.5, 206/581, 812; 229/87.07, 87.08, 87.09, 87.11, 229/117.27, 121
See application file for complete search history.

(56) References Cited

U.S. PATENT DOCUMENTS

| | | | |
|---|---|---|---|
| 2,940,861 A * | 6/1960 | Hultkrans | 229/87.11 |
| 3,557,853 A * | 1/1971 | Jones | 383/86 |
| 4,739,879 A * | 4/1988 | Nakamura | 206/205 |
| 5,076,437 A * | 12/1991 | Schindler | 206/551 |
| 5,193,684 A | 3/1993 | McDonald | |
| 5,261,531 A | 11/1993 | Nieves | |
| 5,579,916 A | 12/1996 | Manko | |
| 5,884,771 A | 3/1999 | McCormick | |
| 5,988,386 A | 11/1999 | Morrow | |
| 6,059,100 A | 5/2000 | Jones | |
| 6,115,997 A | 9/2000 | Burrow et al. | |
| 6,241,147 B1 * | 6/2001 | Guidera | 206/438 |
| 6,702,116 B2 | 3/2004 | Hummel | |
| 6,739,114 B2 | 5/2004 | Shaffer | |

FOREIGN PATENT DOCUMENTS

FR 002698080 A1 * 5/1994
JP 405124676 A * 5/1993

* cited by examiner

*Primary Examiner*—Luan K Bui
(74) *Attorney, Agent, or Firm*—Amin Hallihan, LLC

(57) ABSTRACT

The present invention relates to a storage and waste disposal system designed for use in storage of feminine hygiene products prior to use and for disposal of feminine hygiene products after use. The feminine hygiene product storage and waste disposal system includes a main container having an inner and outer surface and an interior receptacle designed for the storage and waste disposal of feminine hygiene products.

6 Claims, 7 Drawing Sheets

DISPOSABLE FEMININE PROTECTION STORAGE AND WASTE DISPOSAL SYSTEM

FIELD OF THE INVENTION

The present invention relates to a feminine hygiene product storage and waste disposal system. The feminine hygiene product storage and waste disposal system is adapted for use in storage of feminine hygiene products prior to use and for disposal of feminine hygiene products after use. The feminine hygiene product storage and waste disposal system generally comprises a main container having an interior receptacle designed for such use. More particularly, in one preferred embodiment, the main container has an inner and outer surface connected by opposing ends with an interior receptacle comprising a plurality of compartments for handling multiple feminine hygiene products prior to use and after use.

BACKGROUND OF THE INVENTION

Figure 2:
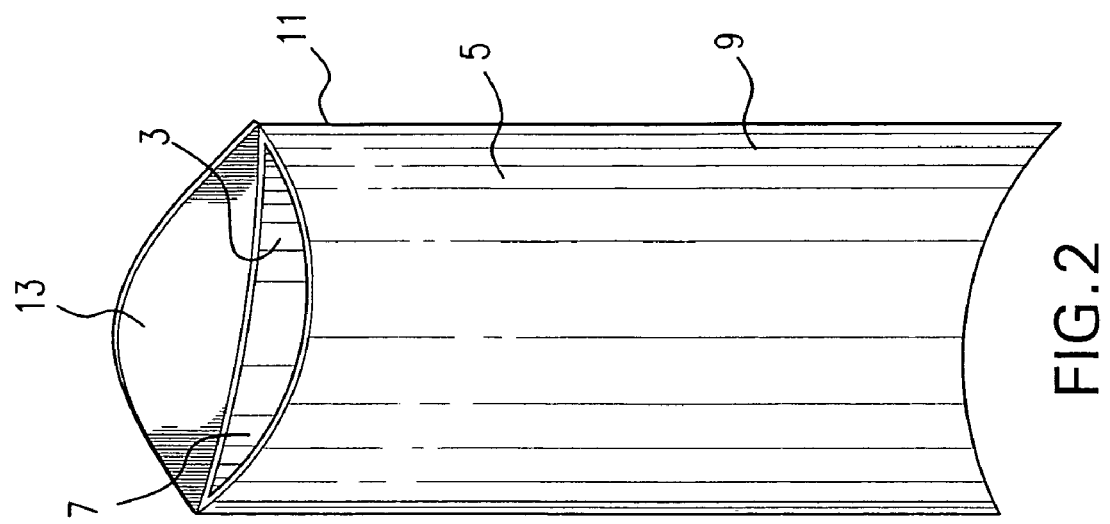
FIG. 2 is a front-facing view of the main container with an end closure extended contiguously outward.

The storage and disposal of feminine hygiene products such as pads, tampons or the like poses a difficult problem for females during menses. Storage of feminine hygiene products often includes placing the product in a purse, bag or similar object until use. The product may be visible when a woman needs to go into her purse for other objects and cause embarrassment or other discomfort. Disposal of feminine hygiene products often causes other obstacles. Often it is difficult to dispose of the products after use, especially when away from home, as public restrooms do not always have adequate disposal facilities such as a tampon disposal container and if you are a guest in someone's home, you may not want to dispose of it there. In the past, women have wrapped the used product in toilet paper or similar material until they can dispose of it in a proper disposal container. This method is not only unsanitary, it can cause embarrassment and social distress as well as creating external problems such as odor and potential health conditions due to the unsanitary method of previous disposal.

A variety of systems exist for storage of feminine hygiene products, such systems being made up of a container, pouch or similar device for storage of single or multiple products. The prior art relating to these storage containers includes specific configurations such as a triangular shape and a hinged clamshell shape. This invention does not relate to a specific configuration, although in one preferred embodiment the invention is of a generally rectangular shape. Products also exist for single storage of feminine hygiene products through use of plastic, paper or similar material covering the single product.

Methods and products for the disposal of feminine hygiene products are also known in the prior art. Most types of disposal systems consist of a disposal bag wherein the user is required to dispose of the product immediately. Storage of used feminine hygiene products for later disposal are not known in the prior art.

There is therefore a need for a feminine hygiene product storage and waste disposal system that incorporates both a compartment for storage of feminine hygiene products prior to use and a compartment for storage for feminine hygiene products after use for immediate disposal, or in the alternative, for later disposal if facilities do not exist for immediate disposal.

SUMMARY OF THE INVENTION

The present invention relates to a feminine hygiene product storage and waste disposal system. The feminine hygiene product storage and waste disposal system is adapted for use in storage of feminine hygiene products prior to use and for disposal of feminine hygiene products after use.

A general object of this invention is for the storage and disposal of feminine hygiene products prior to use and after use.

A more particularized object of this invention is a discrete method of such storage and disposal of feminine hygiene products.

A further object of this invention is to provide minimal embarrassment and distress to the user for storage and disposal of feminine hygiene products.

A further object of this invention is to provide a simple means for the storage and disposal of feminine hygiene products prior to use and after use.

A further object of this invention is to provide a sanitary means of disposal of feminine hygiene products.

A further object of this invention is to provide a feminine hygiene product storage and waste disposal system that is cost-efficient and practical for the user as well as fun and fashionable.

The prior art has generally failed to provide a system for both storage and waste disposal of feminine hygiene products. The prior art has generally failed to provide a feminine hygiene product storage and waste disposal system that provides for a container that is easy to carry and store in its intended location, such as a women's purse, bag, or similar item. The prior art has generally failed to provide a feminine hygiene product storage and waste disposal system that provides a sanitary storage container for feminine hygiene products after use for immediate disposal, or if facilities are not available for immediate disposal, for later disposal at the discretion of the user. There is therefore a need for such an invention that provides a discrete, simple and sanitary method for storage and disposal of feminine hygiene products.

DETAILED DESCRIPTION OF THE INVENTION

The present invention relates to a feminine hygiene product storage and waste disposal system that provides storage of feminine hygiene products prior to use and for waste disposal of feminine hygiene products after use. The disposal of such feminine hygiene products is designed such that the user can immediately dispose of the used product if facilities are available or can store the used product for later disposal if proper facilities are not available, such as in public restrooms, or if the user prefers to wait to dispose of the used product, such as when visiting another person's house.

The present invention is designed to provide a discrete method for storage and disposal of feminine hygiene products prior to use and after use. The invention is such that it fully conceals the feminine hygiene products thereby providing minimal embarrassment and distress often associated with such use. The invention is also designed to provide a simple means of such use while providing a sanitary method for the storage and disposal of the feminine hygiene products. The design of the invention can be such that different patterns, colors, designs, etc. are placed on the invention and a variety of such different patterns, colors, designs, etc. can be utilized so that the user has a wide array of choices to match their personal taste and style.

Figure 1:
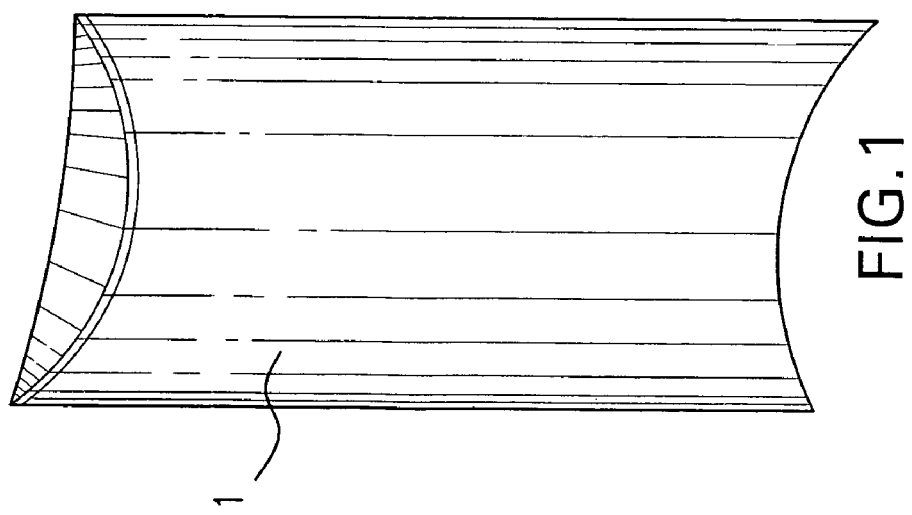
FIG. 1 is a front-facing view of the main container of the feminine hygiene product storage and waste disposal system.
Figure 3:
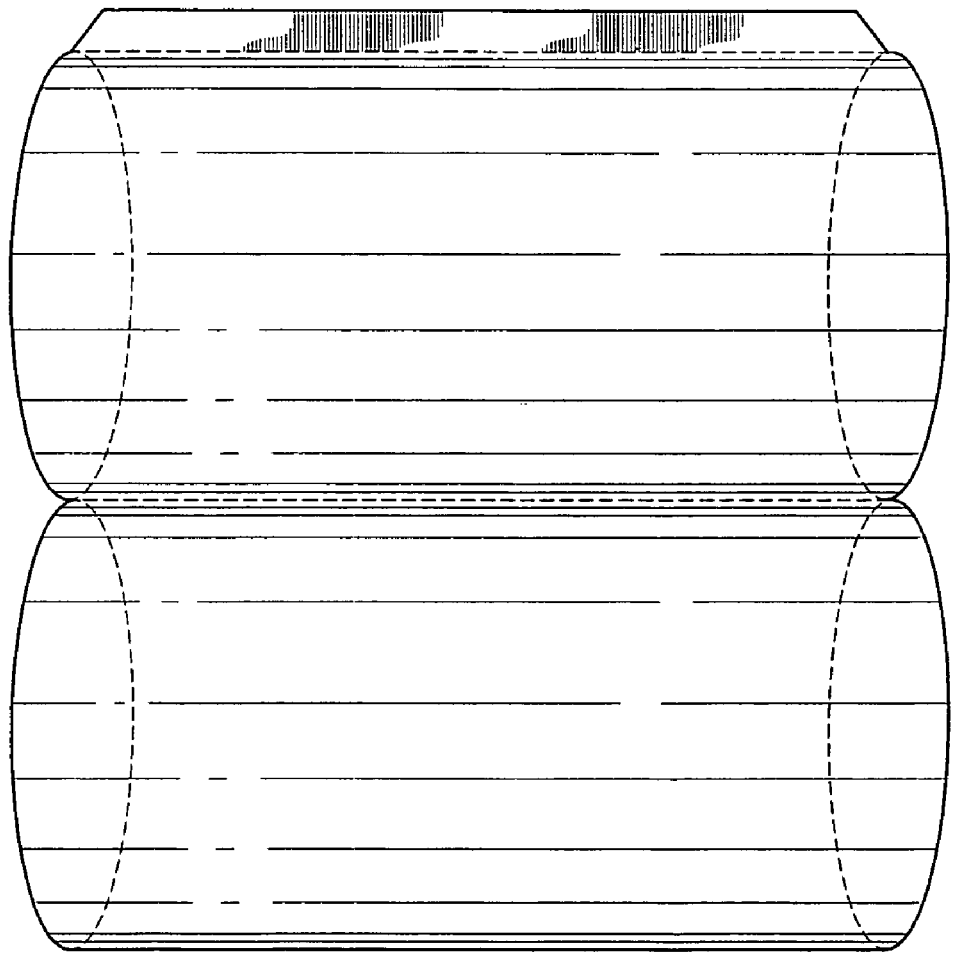
FIG. 3 is a front-facing view of the main container with the top portion and bottom portion of the outer surface detached and open into a two dimensional shape with the end closures extended contiguously outward.
Figure 5:
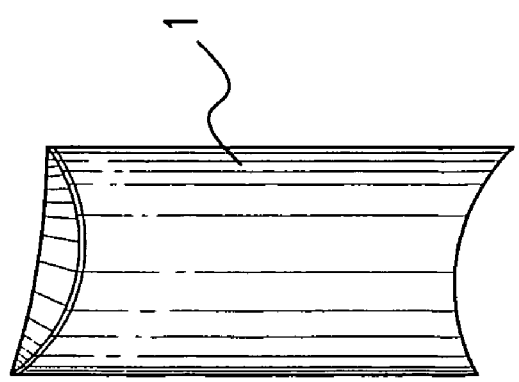
FIG. 5 is a front-facing view of a feminine hygiene product storage and waste disposal system that is shorter by length than the feminine hygiene product storage and waste disposal system shown in FIG. 1.
Figure 6:
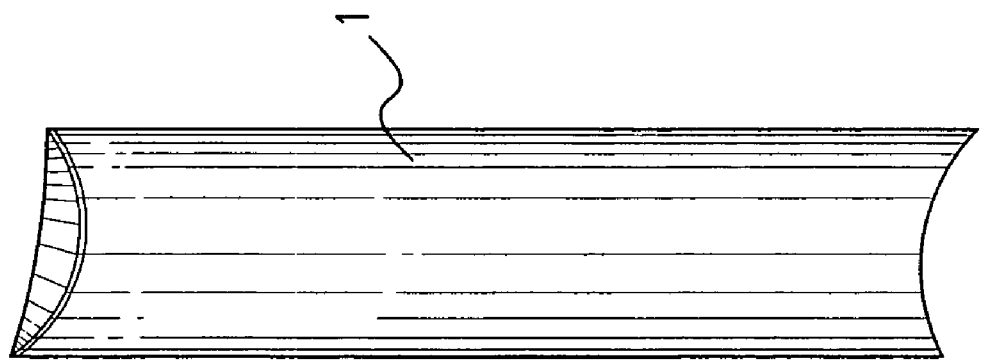
FIG. 6 is a front-facing view of a feminine hygiene product storage and waste disposal system that is less width than the feminine hygiene product storage and waste disposal system shown in FIG. 1.

FIG. 1 illustrates one preferred embodiment of the feminine hygiene product storage and waste disposal system. In this embodiment, the feminine hygiene product storage and waste disposal system generally comprises a main container 1 as shown in FIG. 1 with the main container 1 having an inner surface 3 and an outer surface 5 as illustrated in FIG. 2. The main container 1 has an interior receptacle 7 with the outer surface 5 having a top portion 9 and a bottom portion 11 as illustrated in FIG. 2. FIG. 3 illustrates the main container 1 flattened to a two dimensional shape with the top portion 9 and the bottom portion II of the outer surface 5 detached and open. In this embodiment, the top portion 9 and bottom portion 11 are connectedly attached by end closures. FIG. 2 illustrates one such end closure 13. The end closures extend contiguously outward from the top portion 9 or bottom portion 11, thereby providing a means for closure of the main container 1. In this embodiment, the main container 1 is of a generally rectangular shape and the end closures are shaped such that when the end closures are collapsed to conform to the generally rectangular shape, the end closures are generally concave. Other sizes of this embodiment are shown in FIG. 5 and FIG. 6 with the main container 1 illustrated.

In another preferred embodiment, the end closures are flap-type closures having tabs which fold into the inner surface 3 providing a sealable means when closed. The flap-type enclosures provide openings at either opposing end when open. Alternatively, the end closure on one end is permanently sealed with the opposing flap-type end closure providing an opening to the interior receptacle 7.

Figure 4:
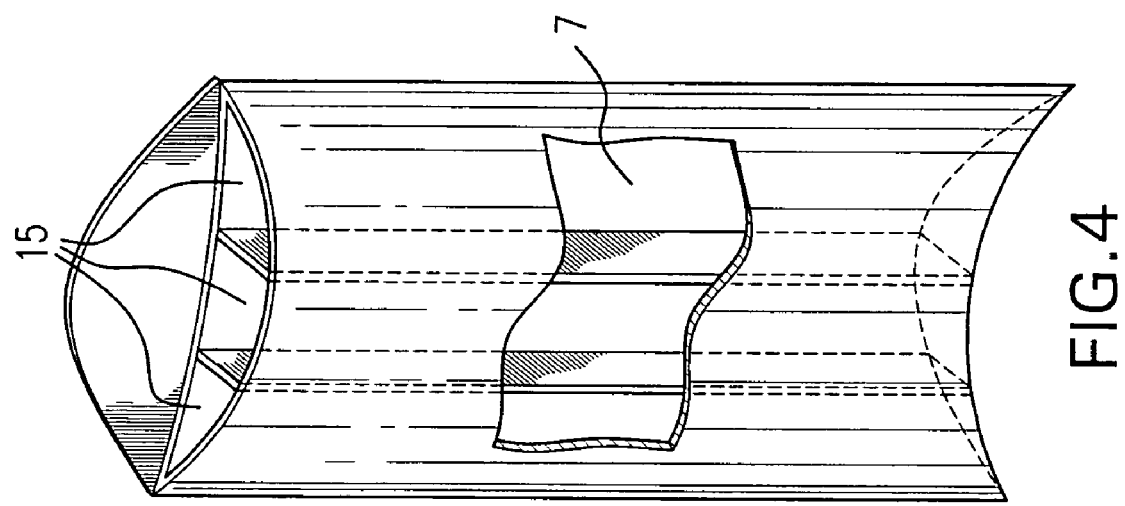
FIG. 4 is a front-facing, cut-away view of the main container with an interior receptacle comprising one or more compartments.

In another preferred embodiment, the interior receptacle 7 comprises one or more compartments 15 that are adapted for storing one or more feminine hygiene products as illustrated in FIG. 4. The one or more compartments 15 provide storage for feminine hygiene products prior to use and the one or more compartments 15 provide storage for feminine hygiene products after use for later disposal.

Figure 7:
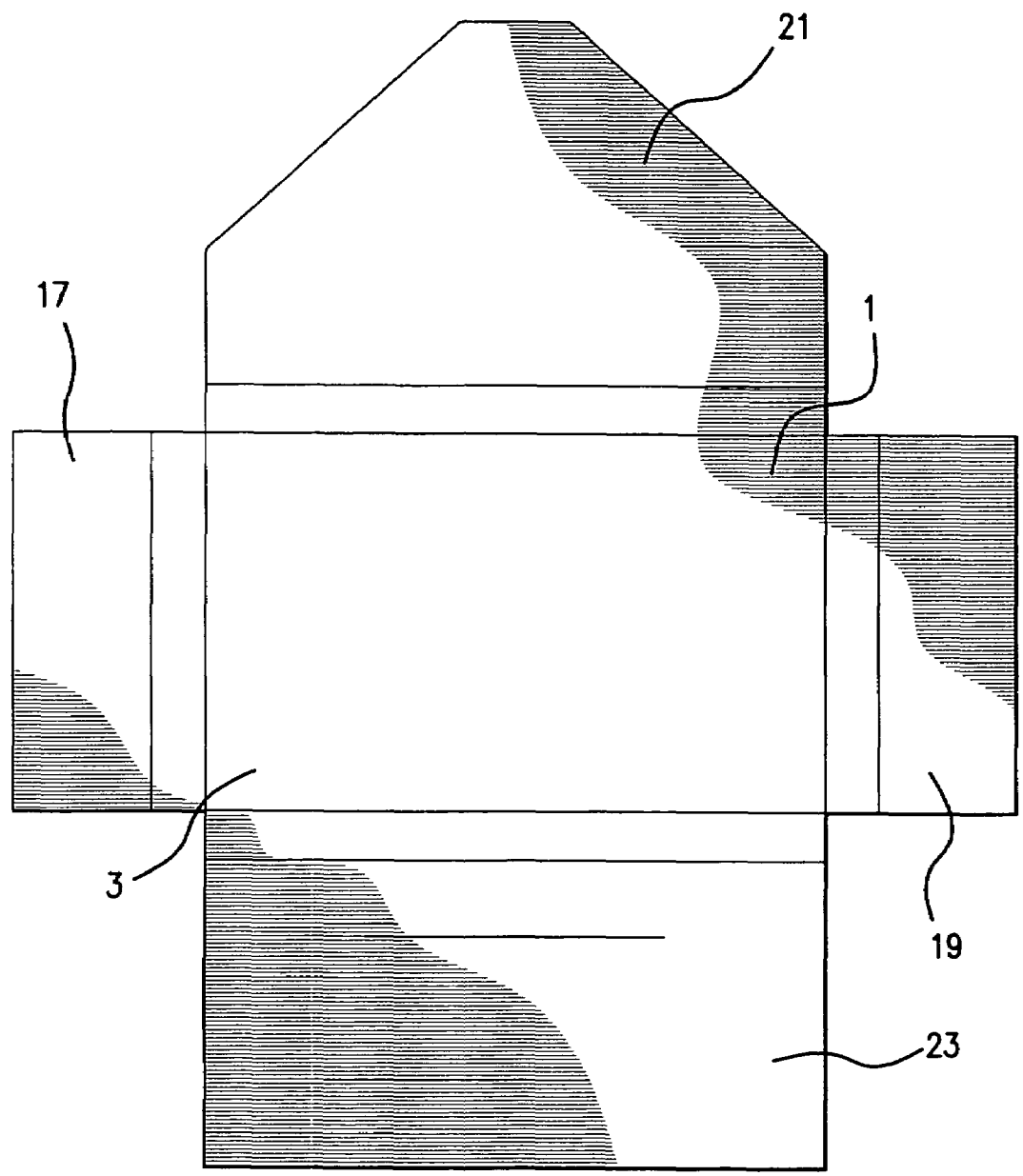
FIG. 7 is a top view of the generally-square shaped main container with the flap-type closures unfolded and open into a two dimensional shape.
Figure 8:
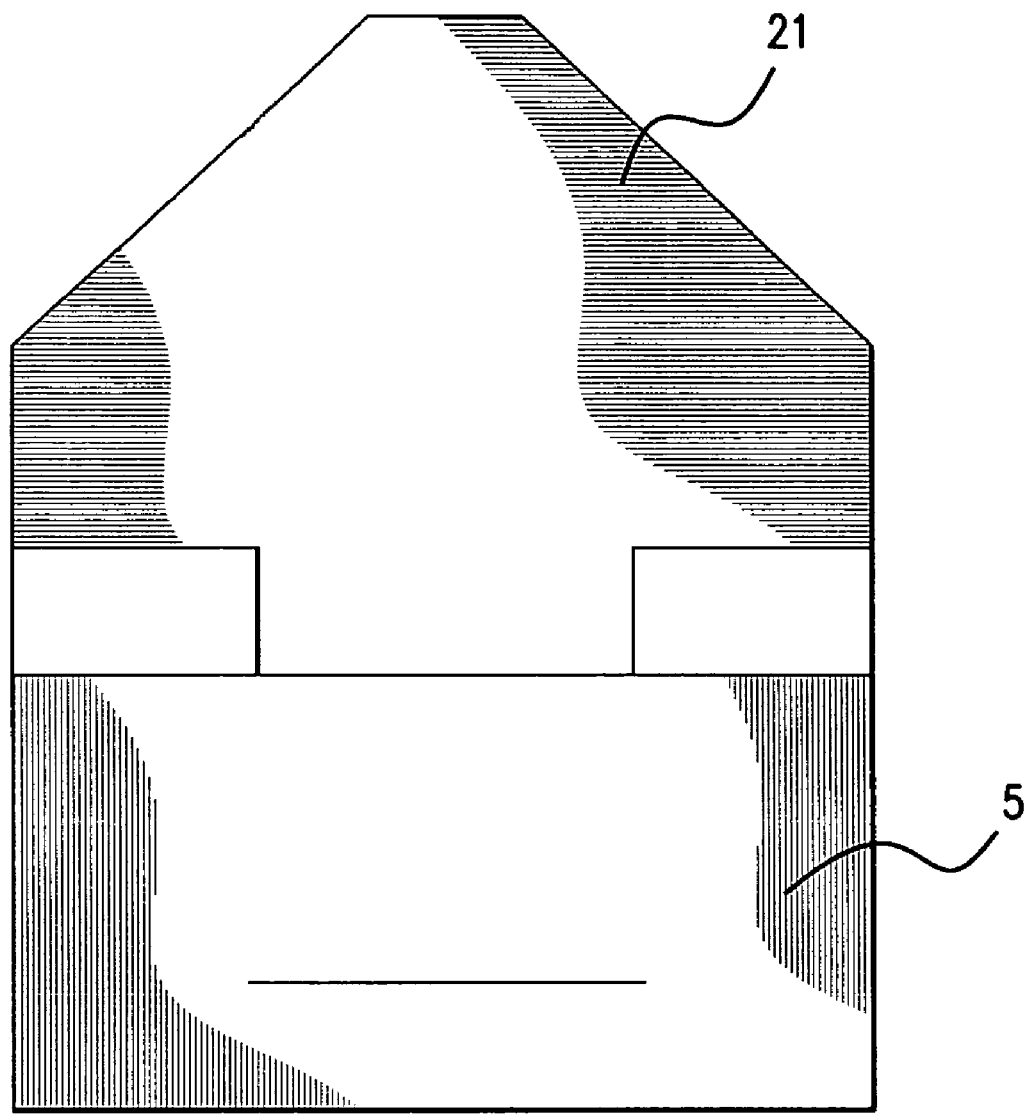
FIG. 8 is a top view of the main container with the top flap closure extended contiguously outward from the outer surface.
Figure 9:
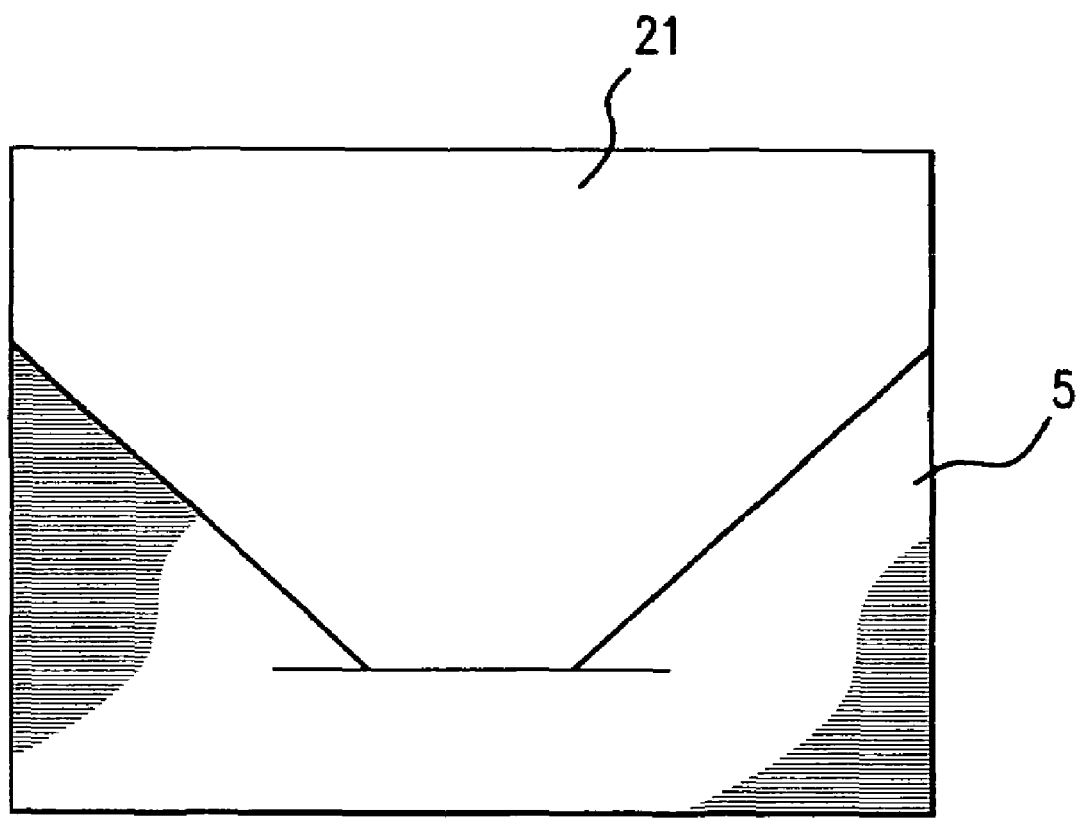
FIG. 9 is a top view of the main container with left side flap closure, right side flap closure and bottom flap closure folded into the inner surface and the top flap closure folded and inserted into the outer surface.

In another preferred embodiment, the main container 1 is of a generally square shape as illustrated in FIG. 7. The main container 1 comprises a left side flap closure 17, a right side flap closure 19, a top flap closure 21, a bottom flap closure 23 and an inner surface 3 as illustrated in FIG. 7. FIG. 7 also illustrates the main container 1 flattened to a two dimensional shape with the flap-type closures unfolded and open. The left side flap closure 17, the right side flap closure 19 and the bottom flap closure 21 fold into the inner surface 3 and the top flap closure 21 folds and inserts into the outer surface 5 providing a sealable means when closed as illustrated in FIG. 9. The top flap closure 21 extends contiguously outward from the outer surface 5 providing an opening as illustrated in FIG. 8.

Any of the embodiments of the present invention described herein may additionally comprise a waterproof lining on the inner surface 3. This waterproof lining provides protection against potential fluid leaks and allows for multiple uses, if so desired.

Any of the embodiments of the present invention described herein may additionally comprise a deodorizing element on the inner surface 3. This deodorizing element provides a sanitary means for the storage and disposal of the feminine hygiene products.

In any of the embodiments of the present invention described herein, the container may additionally flatten to a two dimensional shape, adapted to fold into an inflated shape, thereby providing access to the interior receptacle for the storage and disposal of feminine hygiene products and providing a simple carrying means.

In another preferred embodiment, the opposing end closures are resealable, thereby providing for multiple uses or multiple accesses to the feminine hygiene products stored therein.

In another preferred embodiment, the flap-type closures are resealable, thereby providing for multiple uses or multiple accesses to the feminine hygiene products stored therein.

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

I claim:

1. A feminine hygiene product storage and disposal system, comprising:
    a container adapted for multiple use having an inner surface and an outer surface, said inner surface including a cleanable, waterproof lining;
    said container and having an interior receptacle including at least two compartments;
    said interior receptacle adapted for storing a feminine hygiene product prior to use and after use;
    said container having the outer surface printable with at least one color, pattern, design or combination thereof;
    said container having a top portion and a bottom portion;
    said top portion and said bottom portion connectedly attached by end closures;
    said end closures extending outwards in a contiguous manner from the top or the bottom portion; and
    said end closures adapted to provide a means for sealing the top and bottom portions, thereby closing the inner surface of the container.

2. The feminine hygiene product storage and waste disposal system of claim 1 wherein said compartments are adapted for storing a plurality of feminine hygiene products.

3. The feminine hygiene product storage and waste disposal system of claim 1 wherein said inner surface of said container comprises a deodorizing element.

4. The feminine hygiene product storage and waste disposal system of claim 1 wherein said container is of a generally rectangular shape.

5. The feminine hygiene product storage and waste disposal system of claim 1 wherein said container flattens to a two-dimensional shape, adapted to fold into an inflated shape such that the interior receptacle is adapted for said storage and waste disposal.

6. The feminine hygiene product storage and disposal system of claim 1 wherein said end closures are resealable.

\* \* \* \* \*